Figure 1:
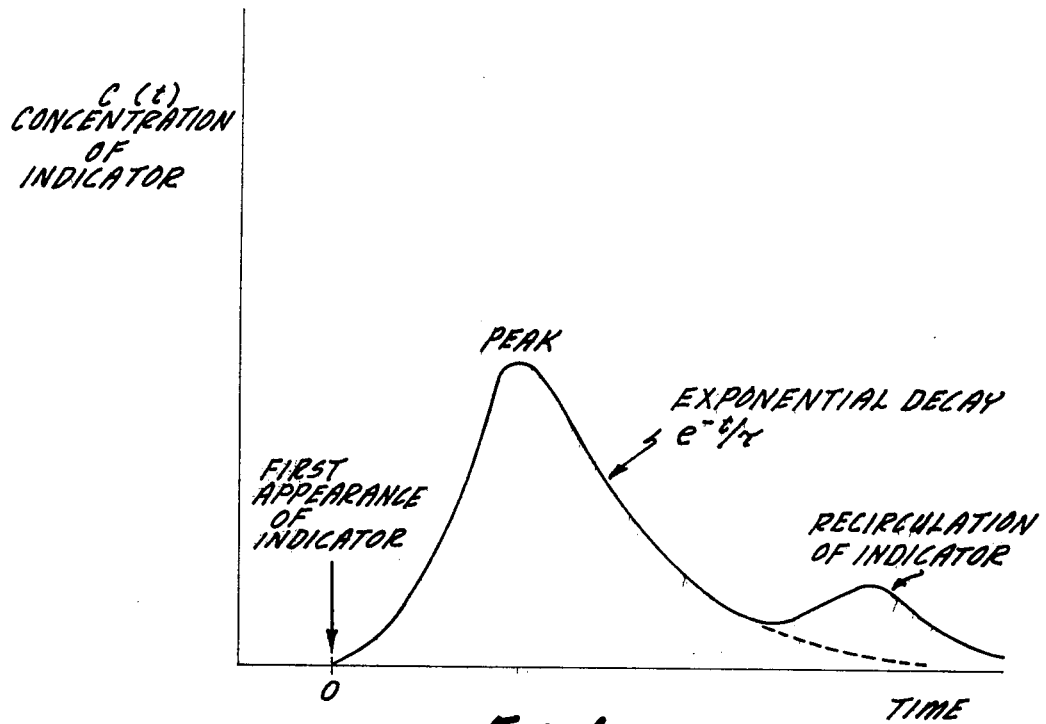

United States Patent [19]

Elings

[11] 4,230,126
[45] Oct. 28, 1980

[54] APPARATUS AND METHOD FOR MEASURING EXTRAVASCULAR LUNG WATER

[76] Inventor: Virgil B. Elings, P.O. Box 6075, Santa Barbara, Calif. 93111

[21] Appl. No.: 962,308

[22] Filed: Nov. 20, 1978

Related U.S. Application Data

[63] Continuation-in-part of Ser. No. 940,114, Sep. 6, 1978, abandoned.

[51] Int. Cl.³ .............................................. A61B 5/08
[52] U.S. Cl. .................................. 128/671; 128/716; 128/692
[58] Field of Search ............... 128/659, 713, 656, 670, 128/671, 716, 630, 692

[56] References Cited

U.S. PATENT DOCUMENTS

| 3,726,269 | 4/1973 | Webster, Jr. | 128/713 |
| 3,987,788 | 10/1976 | Emil | 128/713 |
| 4,004,576 | 1/1977 | Gähwiler | 128/713 |
| 4,015,593 | 4/1977 | Elings, et al. | 128/713 |
| 4,105,022 | 8/1978 | Antoshkiw et al. | 128/713 |

Primary Examiner—Kyle L. Howell

Attorney, Agent, or Firm—Charles H. Schwartz

[57] ABSTRACT

Apparatus for providing a measure of extravascular lung water of a subject using a single thermal indicator, including means for providing an injection of the thermal indicator into the bloodstream of the subject at a position proximal to or in the right heart, means for detecting a first time-temperature concentration curve of the bloodstream at a position in the pulmonary artery, means responsive to the first time-temperature concentration curve detected in the pulmonary artery for calculating a characteristic time for the first time-temperature concentration curve, means for detecting a second time-temperature concentration curve of the bloodstream at a position in a systemic artery, means responsive to the second time-temperature concentration curve detected in the sytemic artery for calculating a characteristic time for the second time-temperature concentration curve, means for calculating the flow of blood through the heart and lungs, and means for calculating a measure of extravascular lung water in accordance with the difference between the products of the blood flow times the first characteristic time and the blood flow times the second characteristic time.

44 Claims, 7 Drawing Figures

APPARATUS AND METHOD FOR MEASURING EXTRAVASCULAR LUNG WATER

This is a continuation-in-part of application Ser. No. 940,114 filed Sept. 6, 1978, and entitled "Apparatus and Method For Measuring Extravascular Lung Water", now abandoned.

The present invention relates to an apparatus and method for measuring extravascular lung mass and specifically extravascular lung water which is a constituent portion of the lung mass. The invention relates to the use of a single thermal indicator for providing for the measurement and which indicator is injected into the bloodstream proximal to or in the right heart and with a detection of the thermal dilution curve produced by the thermal indicator. The thermal dilution curve which represents the temperature versus time characteristics is detected at two locations in the bloodstream and specifically is detected in the pulmonary artery and distal to the left heart in a systemic artery.

In order to provide for the measurement of extravascular lung water, a characteristic time is calculated for the thermal dilution curves in both the pulmonary and systemic arteries. Additionally in a particular embodiment of the invention, the cardiac output or blood flow is determined from the dilution curve in the systemic artery. These particular measurements and resultant calculations are used to calculate the extravascular thermal volume or the extravascular lung water. This calculation is determined generally as the difference between the products of the cardiac output times the characteristic times. The present invention, therefore, provides for the measurement of extravascular lung mass such as lung water by the use of a single thermal indicator whose dilution curve is detected twice in the circulatory system.

Other portions of the present invention include improved methods of measurement and calculation which provide for a more accurate measure of extravascular lung water not only in the preferred embodiment of the present invention but also using prior art methods of determining extravascular lung water.

A determination of extravascular or interstitial water in the lungs is of importance in the diagnosis and treatment of respiratory disorders. The retention of interstitial water in the lungs is generally referred to as pulmonary edema. For example, if a patient is critically ill, it is desirable for the physician to quickly and precisely determine changes in the lung water so as to assess the progress of the patient and, in particular, to determine the effects of any medication given to the patient. Ideally, these measurements would be made on a round-the-clock basis in the hospital's intensive care unit and with the measurements made by nurses or interns with only a minimum of training in the use of an instrument for making the measurement.

The most important aspect of the measurement of extravascular lung water is not an absolute accuracy of the measurement itself, but rather whether the measurement is reproducible on a particular patient and whether the measurement reflects actual changes in the quantity of lung water for that particular patient. Another desirable aspect of any method to be used for providing such a measurement of extravascular lung water would be that the safety of the patient should be assured while the measurement is being made. Preferably, the measurement should be made without the withdrawal of or reinjection of any blood from the patient since such a withdrawal or reinjection of blood might endanger the patient and also might complicate the measurement procedure.

One prior art technique which has been used for the measurement of lung water is generally a double indicator dilution technique. In this prior art technique, two indicators are injected into the patient's blood stream with the injection usually in the vena cava. The concentration of the two indicators as a function of time is then measured in a systemic artery which is usually the aorta.

One of the indicators which is called the intervascular indicator dilutes only with the blood. Specifically, this indicator does not mix with anything outside the blood vessels. As an example, intervascular indicators which have been used are large molecules such as albumin which are tagged with tracers such as a radioactive isotope or tagged with a color dye such as indocyanine green. These tagged molecules are too large to diffuse outside the blood vessels and, therefore, the concentration of the intervascular indicator as a function of time is representative only of the blood.

The other indicator in the double dilution technique is generally called the extravascular indicator and this indicator can diffuse outside the blood vessels and mix with the lung water which surrounds the blood vessels in the lungs. Extravascular indicators that have been previously used are small molecules tagged with a radioactive isotope (such as tritiated water) or heat. Ideally, the extravascular indicator should diffuse easily outside the blood vessels and mix with the lung water.

The dilution curves which are produced and which are, in general, used in the present invention, provide for the curve initially rising to represent a peak concentration and with the curve then having an exponential decay representing a similar decay in the concentration. The dilution curve shows the decay down to a point where the indicator recirculates through the body and therefore reappears as an increase in the dilution curve representing an increase in the concentration due to the recirculation.

Generally with the prior art double dilution technique, a measurement of the mean time is made using the following equation $$\bar{t} = \frac{\int_0^\infty c(t)\, t\, dt}{\int c(t)\, dt}$$

where c(t) is the concentration of the dilution curve in the systemic artery and with this measurement beginning from the first appearance of the curve. This mean time ($\bar{t}$) multiplied by the flow of blood through the heart and lungs will give a measurement of the volume of matter between the injection and detection points with which the indicator has mixed. The flow of blood through the heart and lungs may also be referred to as the cardiac output. For the intervascular indicator, this calculation of volume is a measure of the volume of blood between the injection and detection points. For the extravascular indicator, this calculation of volume is a measure of the volume of blood plus the extravascular water in the lungs. The difference between the volumes calculated from the two indicators is thereby taken as a measure of the extravascular lung water.

There have been studies done as to the use of various types of indicators for the double dilution technique.

For example, in the review article by N. Staub, Physiological Reviews, Vol. 54, pps. 678-811, 1974, the use of tritiated water as an extravascular indicator is shown to give results which are poor. Specifically the results do not agree with actual measurements of lung water such as obtained in dogs by removal of the lungs to make a direct measurement. It is thought that the reason for these poor results is that the diffusion constant of tritiated water is not high enough for the indicator to mix well with the extravascular water. On the other hand, other studies have shown that the use of heat as the extravascular indicator and the use of green dye as the intervascular indicator give results which have agreed well with direct measurements.

Heat makes a better extravascular indicator than tritiated water because the diffusion constant of heat is one hundred times the diffusion constant of a small molecule such as tritiated water. Another advantage of the use of heat as an indicator is that the measurement of its concentration is actually a temperature measurement and this may be measured such as with a thermistor on the end of a catheter placed in the blood vessel. In this way, the measurement of the heat concentration can be accomplished without withdrawing blood to determine the indicator concentration. The dilution curves of indicators such as green dye or radioactive isotope tagged molecules require that the blood be withdrawn from the patient and that the concentration then be measured with equipment external to the patient. Each such measurement may require the withdrawal of up to thirty (30) ccs. of blood. After the measurement, the blood is then reinfused into the patient. It can be seen that the withdrawal of blood makes for a much more difficult and also dangerous type of measurement than a thermal measurement which can be made in situ in the blood vessel.

Generally, all of the prior art measurements of lung water have required the use of two indicators and specifically include the use of an intervascular indicator and an extravascular indicator. In addition, the measurement of one of the indicators required the withdrawal of blood from the patient with the measurement then made in equipment external to the patient. The present invention is, however, directed to a system for providing measurements of lung water which uses a single thermal indicator the dilution curve of which is sensed at two points in the circulatory system and with the preferred embodiment of the system of the present invention no blood is withdrawn from the patient.

As indicated earlier, the dilution curve may have a mean time calculated from the equation which was defined above. In addition, the dilution curve may have another characteristic time which is defined as the exponential decay time $\tau$. The standard theory states that if a fluid is flowing into a chamber of volume V and an indicator is injected into the fluid upstream from the chamber, the dilution curve measured downstream from the chamber will have an exponential decay and with the decay time given by the relationship $\tau = V/F$ where F is the flow of fluid in units of volume/time. The volume of the chamber, therefore, can be determined from the decay time of the dilution curve and the flow of the fluid. The flow of the fluid F can be determined from the reciprocal of the time integral of the dilution curve, which is $$F = \frac{\text{constant}}{\int_0^\infty c(t)dt}$$

If the indicator which is being measured flows through several chambers, the decay of the dilution curve downstream from the chambers is a sum of exponentials. Therefore, the decay portion of the curve has the mathematical form $$Ae^{-t/\tau_1} + Be^{-t/\tau_2} + Ce^{-t/\tau_3} + \ldots$$

where
$\tau_1 = (V1/F)$; $\tau_2 = (V2/F)$; etc.
where
$V_1$ = volume of first chamber
$V_2$ = volume of second chamber, etc.
where
F = the flow which is the same for all chambers.

If one of the chambers is much larger than the others, then this chamber will dominate the decay of the curve. Therefore, well down from the peak of the curve, the curve will essentially become a single exponential with the decay time determined by the large chamber. This relationship may therefore be used in a particular embodiment of the invention wherein the extravascular lung water as measured using a characteristic time and with this characteristac time specifically being the decay tame.

The use of heat as an indicator does have disadvantages as well as advantages. These disadvantages relate not only to the use of heat as an indicator in the present invention but also to the use of heat as an indicator in the prior art double dilution technique. The present invention therefore provides for improvements in the use of heat as an indicator for both the prior art techniques and the techniques described in the present invention.

There are a number of drawbacks in the use of heat as an indicator when measuring extravascular lung water. First, some of the heat indicator can be lost to the air in the lungs and is therefore not detected in the dilution curve in the systemic artery. This loss will vary from patient to patient and also whether the patient is placed on a respirator or not.

Second, the thermal dilution curve in the systemic artery is not a large signal and generally is about one-quarter degree centigrade at its peak. This signal may thereafter be easily affected by temperature drifts of the patient during the measurement or changes in the temperature of the blood during the respiratory cycle. The smallness of the signal makes it difficult to make good calculations of either the mean time of the curve or the area under the curve. Because of these problems, the prior art generally calculated the cardiac output from the indocyanine dye curve when using the double indicator technique with heat and indocyanine dye as the two indicators. Sometimes, the average of the cardiac output is calculated from the thermal dilution and dye curves. However, the dye curves are used as part of this calculation since the dye curves are not susceptible to the problems indicated above.

When heat is used as the extravascular indicator, the more common "measure of lung water" which appears in the literature is a quantity called the Extravascular Thermal Volume (EVTV) and is calculated in the following manner:

EVTV = Cardiac Output × mean time of the thermal curve − Cardiac Output × mean time of the intervascular indicator curve Although this quantity has units of volume, it is not the actual volume of extravascular lung water (EVLW). The actual volume of extravascular lung water, assuming that all of the extravascular mass is water, is calculated by the formula:

$EVLW$ = (Cardiac Output × mean time of thermal curve − Cardiac Output × mean time of intervascular indicator curve) × $\frac{\text{Volume specific heat of blood}}{\text{Volume specific heat of water}}$ =

$EVTV \times \frac{\text{Volume specific heat of blood}}{\text{Volume specific heat of water}}$ The ratio of the volume specific heat of blood to that of water varies little from patient to patient and has the value of 0.93. Essentially then, the calculation of extravascular thermal volume and extravascular lung water are the same except for a constant. In the present disclosure we discuss computing the extravascular thermal volume, but it must be appreciated that we could multiply by a constant to obtain the extravascular lung water.

The expression for calculating the cardiac output from a thermal dilution curve is given in the literature as $$\text{cardiac output} = \frac{V_I \times (T_B - T_I) \times C_I}{C_B \times \int \Delta T(t)dt}$$

wherein
$V_I$ = volume of injectate.
$T_I$ = temperature of injectate
$T_B$ = temperature of blood
$C_I$ = volume specific heat of injectate
$C_B$ = volume specific heat of blood
$\int \Delta T_B(t)dt$ = area under the thermodilution curve
In addition, we define the quantity, $$A = V_I \times (T_B - T_I) \times \frac{C_I}{C_B}$$

which we call the amount of thermal injectate. One should note that the calculation of the cardiac output is inversely proportional to the area under the thermodilution curve.

An advantage of the use of the thermal measurements of the present invention is that the product of the cardiac output determined from a thermal dilution curve times a characteristic time for the same curve provides for compensation for a drifting baseline.

Figure 2:
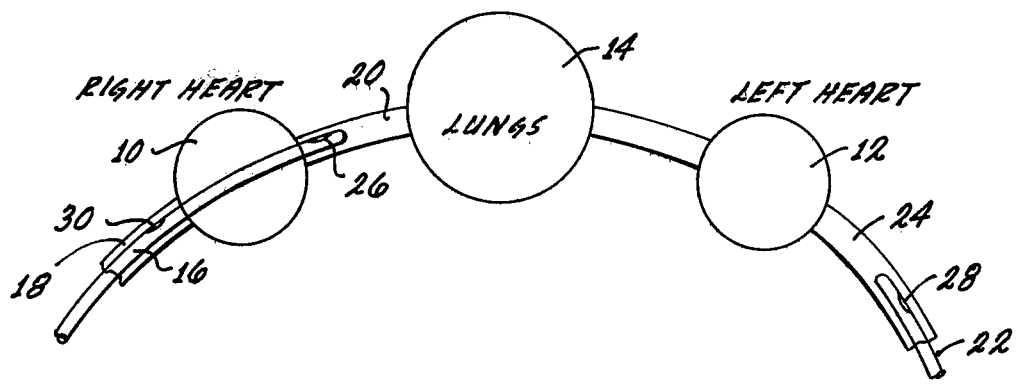
Figure 3:
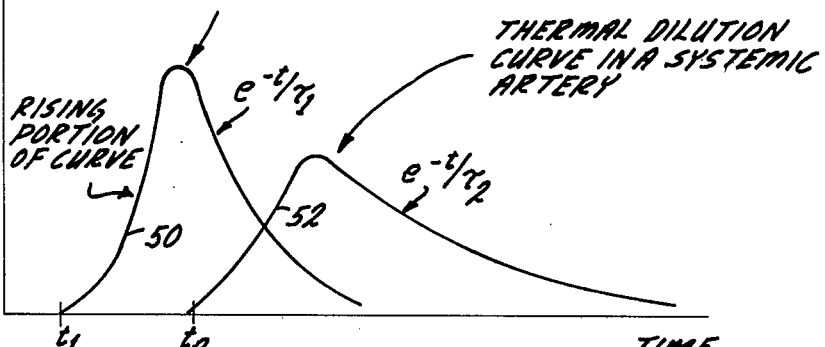
Figure 5:
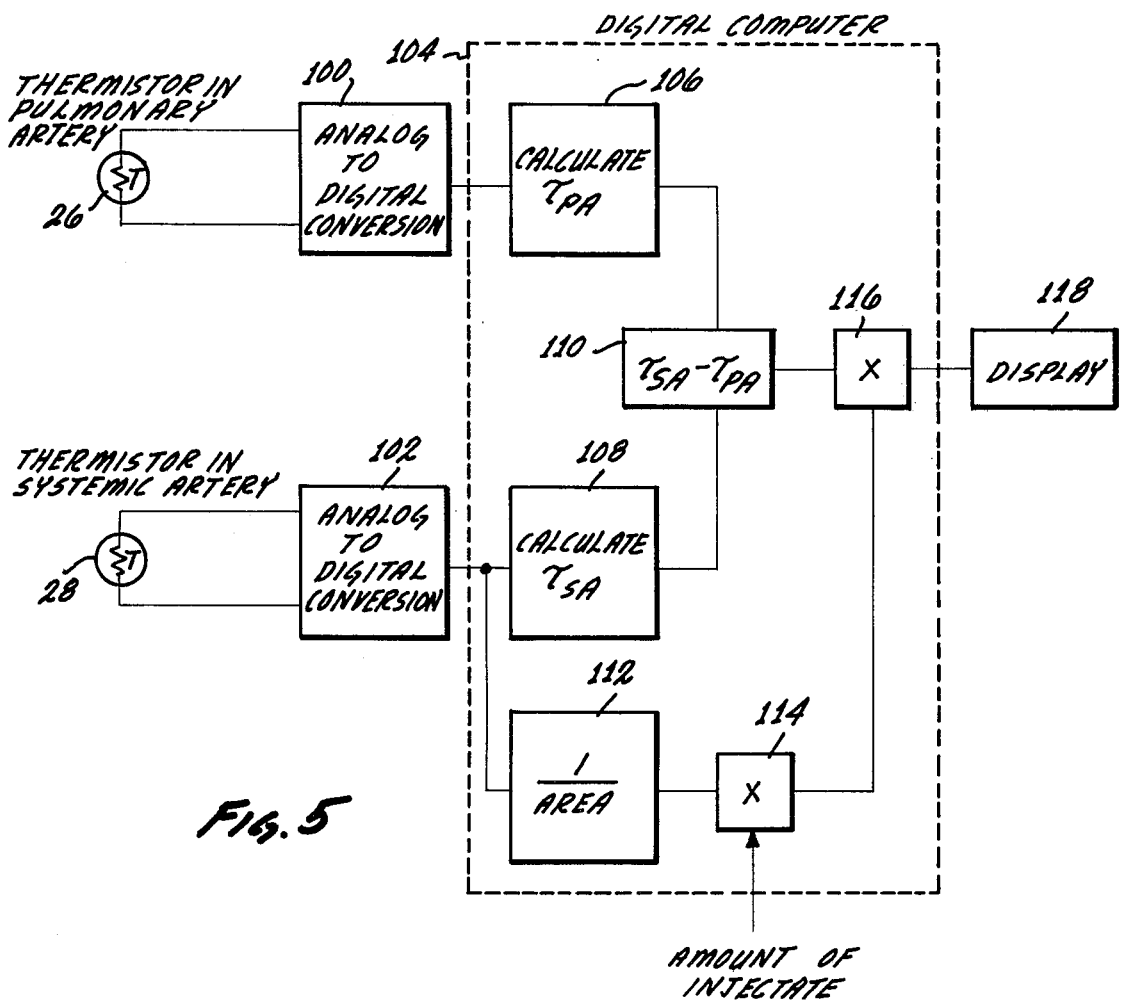
Figure 4:
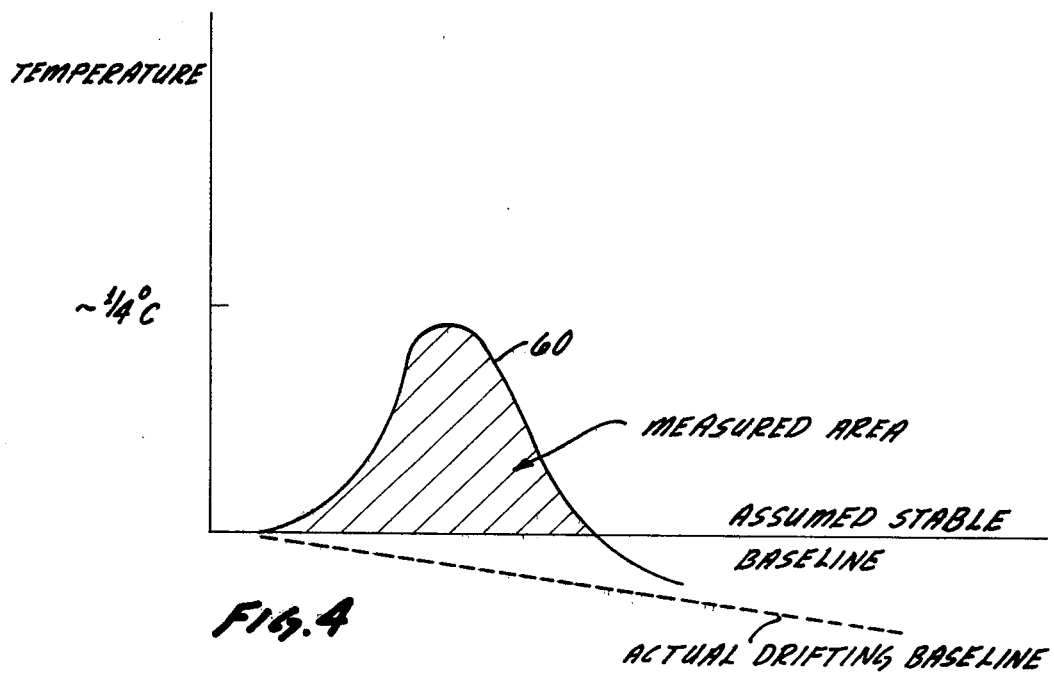
Figure 6:
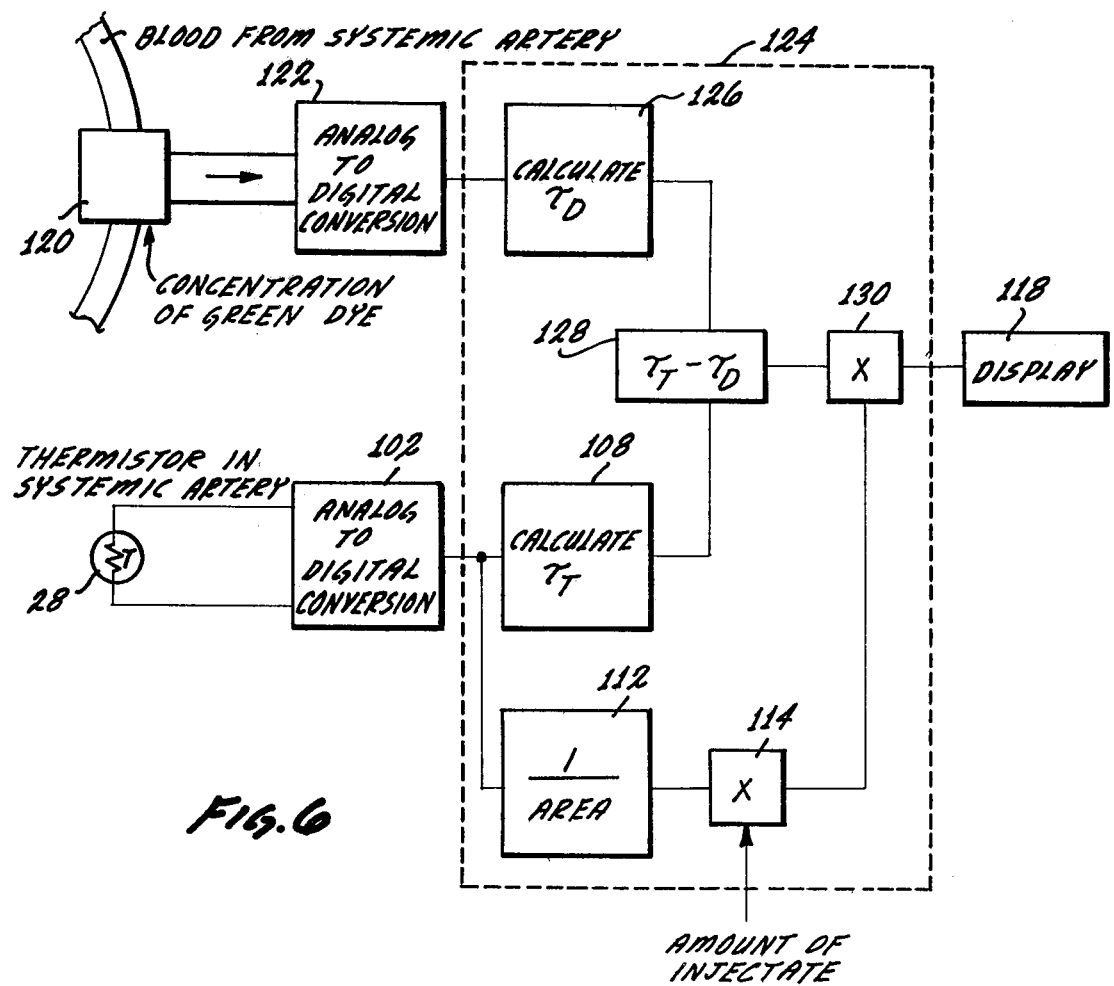
Figure 7:
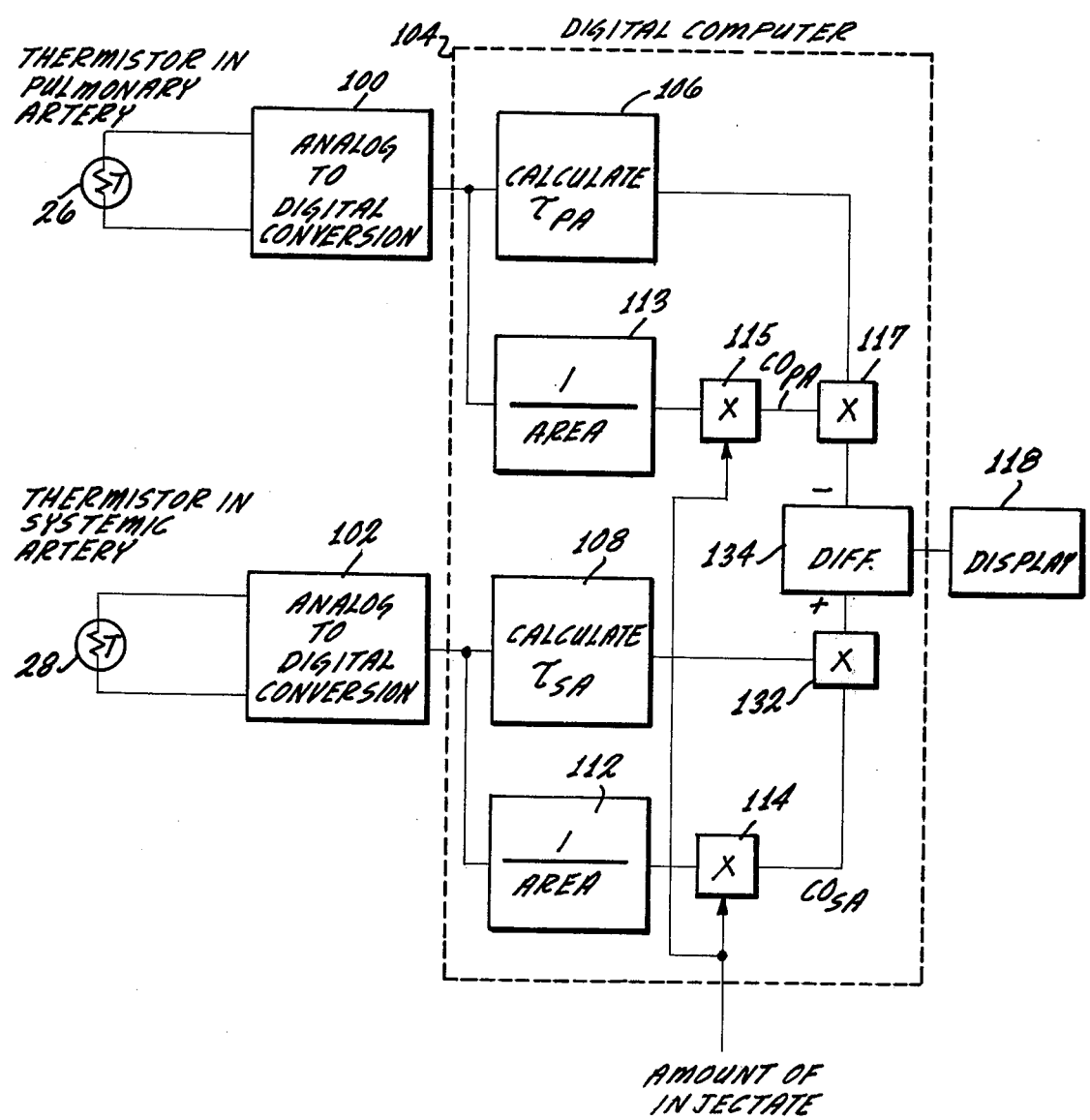

A clearer understanding of the invention will be had with reference to the following description and drawings wherein:

FIG. 1 illustrates a typical indicator dilution curve;
FIG. 2 illustrates a method for providing for the measurement of temperature dilution characteristics using a single thermal indicator to provide for the calculation of lung water;
FIG. 3 illustrates the thermal dilution curves measured from the injection of a single thermal indicator and using the method shown in FIG. 2;
FIG. 4 illustrates a dilution curve with a drifting baseline;
FIG. 5 illustrates a diagram of a system for providing a calculation of lung water using a single thermal indicator;
FIG. 6 illustrates a diagram of a system for providing a calculation of lung water using two indicators but providing for compensation for a drifting baseline temperature of the patient; and
FIG. 7 illustrates a diagram of a different embodiment of a system for providing a calculation of lung water using a single thermal indicator.

FIG. 1 illustrates a typical dilution curve and represents the change in the concentration of the indicator in the fluid being measured v. time. As can be seen from the curve of FIG. 1, the curve rises to a peak concentration and then has an exponential decay which has the form $e^{-t/\tau}$ as shown in FIG. 1. The curve decays down to a point where the indicator recirculates through the body and therefore provides for a rise in the measurement of the concentration of the indicator. The curve without recirculation would be as shown by the dotted line.

The type of dilution curve shown in FIG. 1 is representative of a curve which will occur no matter what type of indicator is used. For example, similar dilution curves will be produced if the indicator is green dye or is a thermal indicator. In addition, one can measure the mean time as defined above and either the mean time or the decay time, both of which are generally referred to as characteristic times, may be used to provide for the calculation of extravascular lung water.

In FIG. 2, a preferred apparatus and method is shown for providing for a measurement of lung water using only a single thermal indicator. FIG. 2 schematically shows the cardiovascular system including the right heart 10, the left heart 12 and the lungs 14. A first catheter 16 may be inserted into a vein 18, through the right heart 10 and into the pulmonary artery 20. A second catheter 22 may be inserted into and positioned within a systemic artery 24 which is distal to the left heart 12.

Both catheters 16 and 22 have temperature sensitive devices mounted at or near their ends, such as thermistors 26 and 28, to provide for a measurement of the temperature of the blood. The thermistors individually monitor the temperature and provide for detection of the dilution curve both in the pulmonary artery 20 and in the systemic artery 24. The thermistors 26 and 28 are connected as part of a processor which is shown in FIGS. 5 and 7 and which processor provides for the various calculations of the dilution curves to produce the measure of extravascular lung water.

The catheter 16 which is inserted through the right heart also has an injection orifice 30 which is located at a position along the catheter before the position of the thermistor 26. As shown in FIG. 2, the injection orifice 30 is usually located proximal to the right heart 10. This injection orifice is used to provide for an injection of the indicator which may be, for example, ten (10) ccs. of a cold five percent (5%) dextrose solution and with the injection occurring into the bloodstream proximal to or in the right heart.

Such a catheter 16 is now in wide use and is commonly called a Swan-Ganz catheter. This type of catheter may already be positioned in the patient for providing for a monitoring of the cardiac output. However, such a catheter has not been used for providing for a measurement of lung water using a single thermal indicator. In addition, the combination of the catheters 16 and 22 both with temperature sensitive devices has not been used for providing for a measurement of lung water. It can be seen, therefore, that when the indicator is injected into the blood through the orifice 30, the temperature measuring devices such as the thermistors 26 and 28 provide for measurement of the temperature in the pulmonary and systemic arteries.

FIG. 3 is a diagram of the time-temperature or thermal dilution curves which would be produced from the two thermistors 26 and 28. The first curve 50 represents the thermal dilution curve in the pulmonary artery and the second curve 52 represents the thermal dilution curve in the systemic artery. As can be seen from FIG. 3, both of these curves follow the general shape of the dilution curve shown in FIG. 1 in that they both rise to a peak and then have an exponential decay as shown in FIG. 3.

As indicated above, the apparatus and method of the present invention for providing for a measure of lung water is to obtain a characteristic time from each of the curves 50 and 52 and to multiply these times by the blood flow and then take the difference between these products to obtain a measure of the lung water which may be either the extravascular thermal volume or the lung water volume depending on the specific calculation.

This measurement of the lung water, using a single indicator, may overestimate the actual EVTV or EVLW, but the difference will be the same for measurements taken at different times. Therefore the change in the measure of lung water for measurements taken at different times would represent an accurate change in the lung water itself. The characteristic time may be either the mean time of the curve or the exponential decay time of the curve. The following analysis of the measure of lung water is given first using the mean time of the dilution curve and second using the exponential decay time of the dilution curve.

The mean time of a dilution curve such as those shown in FIG. 3 is defined as $$\bar{t} = \frac{\int_{t_0}^{\infty} tc(t)dt}{\int_{t_0}^{\infty} c(t)dt}$$

where c(t) is the concentration of indicators, t is the time, and $t_0$ is the time at which the curve begins. For example, in FIG. 3, the pulmonary artery curve begins at $t_0 = t_1$ and the systemic artery curve beginning at $t_0 = t_2$.

As explained above, the standard theory indicates that the mean time of a thermal dilution curve multiplied times the flow or cardiac output gives the thermal volume of material between the injection and detection sites with which the indicator mixes, plus a term which depends on how quickly the indicator was injected into the blood. It has been recognized that one can vary the mean time of the dilution curve by varying the speed of injection which, in turn, varies the time of the rising portion of the dilution curve. Therefore, if a consistent measure of dilution volume is to be made, the method of calculation must provide for the elimination of the term representative of injection time.

In our particular example, the mean time of the systemic arterial curve multiplied by the flow gives the following:

$\bar{t}_{SA} \times F_2 =$ volume of blood in the right heart + volume of blood in the lungs + thermal volume of interstitial water in the lungs + volume of blood in the left heart + I where I = term which depends on injection rate $$\text{thermal volume} = \text{volume} \times \frac{\text{volume specific heat of water}}{\text{volume specific heat of blood}}$$

The mean time of the pulmonary arterial dilution curve multiplied by the flow gives the following expression:

$\bar{t}_{PA} \times F_1 =$ volume of blood in the right heart + I

The difference between the two products is a measure of lung water and is as follows:

Measure of lung water $= \bar{t}_{SA} \times F_2 - \bar{t}_{PA} \times F_1 =$ volume of blood in lungs + thermal volume of interstitial water in the lungs + volume of blood in the left heart Because there are many ways to determine the flow or cardiac output, the flows $F_1$ and $F_2$ in the above expression have been labeled in order to indicate that they may have been determined by different means. For instance, one particular embodiment of the apparatus and method is that $F_1$ is determined from the thermal dilution curve in the pulmonary artery and $F_2$ is determined from the thermal dilution curve in the systemic artery. $F_1$ and $F_2$ may also be determined by the same means.

It can be seen that the measure of lung water is not dependent upon the injection rate since these terms cancel and the laboratory data has verified that the measure is not dependent upon the injection rate. In addition, the measure of lung water defined above clearly overestimates the thermal volume of interstitial water in the lungs since it contains the blood volume of the lungs and of the left heart, but since the volume of blood in the lungs and left heart remain relatively constant for a given subject, the changes in this above measure of lung water is representative of changes in the lung water of the subject. As indicated above, it is the changes in the lung water which are important in assessing the progress of the patient.

The other characteristic time which may be used for providing for a measure of lung water is the exponential decay time. The falling portion of the dilution curve, before recirculation occurs, is an exponential of the form $e^{-t/\tau}$ where $\tau$ is the exponential decay time. As described above, the standard theory states that if the indicator has gone through one chamber of volume V, the decay time is given by $\tau = V/F$ or $V = \tau \times F$. For the dilution curve in the pulmonary artery, the decay time times flow gives the volume of blood in the right heart as defined in the following expression:

$\tau_{PA} \times F_1 =$ volume of blood in right heart

If the indicator passes through more than one volume then, as described above, the standard theory states that the falling portion of the curve is the sum of the exponential decays with the slowest decay being due to the largest chamber. For the dilution curve which is measured in the systemic artery, the decay of the curve is dominated by the largest chamber which is the lungs and includes both the volume of blood and water. Therefore, for the dilution curve in the systemic artery, the decay time times the flow gives the following expression:

$$\tau_{SA} \times F_2 = \text{volume of blood in the lungs} + \text{thermal volume of water in the lungs}$$

The difference in the products of the decay times from the systemic and pulmonary artery curves multiplied by the flow gives a measure of lung water as follows:

Measure of lung water $= \tau_{SA} \times F_2 - \tau_{PA} \times F_1 =$ thermal volume of water in lungs + (volume of blood in lungs − volume of blood in right heart)

Experimental data indicate that this measure of lung water using decay times is typically up to ten percent (10%) larger than the actual thermal volume of lung water and accurately reflect changes in the thermal volume of lung water for a given subject. The second term in the expression given above for the measure of lung water is therefore relatively small and has been found to be constant for each given subject.

It has also been found that the decay times of two dilution curves vary slightly with the rate at which the indicator is injected but the difference between the decay times is not sensitive to injection rate and, therefore, the above measure of lung water is reproducible from injection to injection for any given subject. Although the characteristic time used to provide for the measure of lung water may be any characteristic time which is representative of the dilution curve, the use of the decay time is preferable since this gives a measure of lung water which is only slightly larger than actual lung water and accurately reflects changes in lung water.

In the above-described calculations for providing a measure of lung water, the flow, which in our case is cardiac output, may be determined in a number of ways. In the preferred embodiment using a single thermal indicator, the flow is determined from the reciprocal of the time integral of the dilution curve as shown in FIG. 3. Such thermal dilution curves are susceptible to baseline drifts and FIG. 4 illustrates a thermal dilution curve 60 having such a baseline temperature drift.

The baseline drift may occur from an actual drift in the baseline temperature of a patient or may occur from an electronic drift in the measuring equipment and in either case the drift would be superimposed on the dilution curve. FIG. 4 specifically shows such a curve in the systemic artery which has a maximum temperature variation of approximately one-quarter degree centigrade at its peak and it is obvious that it does not require a very large temperature drift to affect this dilution curve.

Since the measurement equipment assumes a stable baseline, the calculation of a characteristic time is for the dilution curve with no baseline drift. Therefore, the actual drifting baseline makes a curve appear to decrease more quickly than it would if the baseline were not drifting. For example, for the curve shown in FIG. 4, if the calculation is a mean time calculation, this mean time would be shorter than it should be.

The decreased mean time for the curve would, when multiplied by the actual blood flow, give a lung water calculation which is too small. This smaller than actual lung water calculation would also be true if the characteristic time were a decay time since this decay time would be calculated from a curve which would appear to decrease more quickly than it actually is decreasing.

If we still assume a stable baseline, the measured area under the dilution curve which would be the area between the curve and the assumed baseline, is less than the actual area under the curve which would be the area between the curve and the drifting baseline as shown in FIG. 4. If we calculate the cardiac output or flow as proportional to the inverse of the measured area, and since the drift would cause the measured area to be falsely low, then the cardiac output will be falsely high. Therefore, the measurement of cardiac output from the dilution curve shown in FIG. 4 is also subject to small baseline drifts due to actual changes in the patient or electronic drifts.

For the particular example shown in FIG. 4, the baseline drift has an opposite effect on the calculated characteristic time relative to the calculated cardiac output, both calculated from the same curve. In one case, it is falsely shortened and in the other case it is falsely increased. Since the measure of lung water is a product of the flow times characteristic time, these two effects tend to compensate for each other to give a volume calculation of lung water which is less sensitive to drifts than either the calculation of flow or characteristic time.

The characteristic times and cardiac output calculated from the thermal dilution curve in the pulmonary artery are also affected in a similar way by baseline drifts, but to a smaller degree. This is because the pulmonary artery curve is larger in amplitude and shorter in duration than the systemic arterial curve, and therefore the same baseline drift applied to both curves would have a much larger effect on the systemic artery curve, i.e., the effect of the baseline drift increases as the amplitude of the thermal dilution curve decreases.

In one embodiment of the apparatus and method, using a single thermal indicator, the sensitivity to baseline drifts in both the pulmonary artery and systemic artery thermal curves is decreased by calculating the flow from each of the curves and calculating lung water as:

measure of lung water $= F_2 \times$ characteristic time of systemic artery curve $- F_1 \times$ characteristic time of pulmonary artery curve where $F_2$ is the flow or cardiac output calculated from the systemic artery thermal dilution curve and $F_1$ is the flow or cardiac output calculated from the pulmonary artery curve.

In a somewhat simpler embodiment which reduces the sensitivity to the baseline drift in the systemic arterial curve, the cardiac output is calculated only from the systemic arterial thermal curve and is used in the calculation of lung water, i.e., lung water = (characteristic time of systemic arterial curve − characteristic time of pulmonary artery curve) × flow calculated from systemic arterial curve.

This decreased sensitivity to drift in the systemic arterial thermal curve by using the cardiac output calculated from that curve is also true in the double dilution technique when heat is used as the extravascular indicator.

In addition to the above drifts in baseline, it has been determined that some of the heat indicator is lost to the air in the lungs and would therefore not be detected as part of the dilution curve measured in the systemic artery. This loss of the heat indicator will provide for two effects. First, the area of the curve is again reduced giving a falsely high cardiac output measured from the dilution curve. Second, the characteristic times such as the mean time and decay time would be shortened. However, the product of the cardiac output times characteristic time which is used to provide for the calculation of lung water would in general produce a cancellation of these effects. In this way the calculation of lung water is not as sensitive to the loss of heat indicator, since the two effects tend to compensate each other. This again provides for an advantage in using the systemic artery dilution curve to provide for the calculation of cardiac output and this advantage is true for both the single indicator method disclosed as the preferred embodiment of the present invention and the prior art double dilution technique when heat is the extravascular indicator.

FIGS. 5, 6 and 7 illustrate block diagrams of particular devices which are used to compute extravascular lung water and with FIGS. 5 and 7 providing for the calculation using a single thermal indicator and FIG. 6 providing for the calculation using the improved techniques of the present invention as applied to the prior art use of two indicators. In FIG. 5, the thermistors 26 and 28 provide for resistance changes in accordance with changes in temperature in the pulmonary and systemic arteries. The changes in resistance are used as input signals to analog to digital converters 100 and 102. A digital computer 104 such as a microprocessor is shown to encompass the various components within the dotted lines and the digital computer provides for the desired calculations. The actual changes in resistance of the thermistors 26 and 28 are converted to the digital signals by the analog to digital converters 100 and 102 and with these digital signals operated upon by the digital computer 104.

As shown in the system of FIG. 5, the specific component portions of the digital computer include calculations of the exponential decay times of the dilution curves in the pulmonary and systemic arteries. However, it is to be appreciated that any characteristic time of the curves may be used and specifically the digital computer could provide for a calculation of the mean times of the dilution curves instead of the decay times.

The digital computer 104 provides for a calculation of the decay times as shown by component portions 106 and 108. The component 106 provides for calculation of the exponential decay time of the dilution curve in the pulmonary artery and the component 108 provides for calculation of the exponential decay time of the dilution curve in the systemic artery. The difference between these exponential decay times is calculated as shown by component 110 of the digital computer.

The digital computer 104 also provides a calculation of the inverse of the area under the systemic artery dilution curve and this calculation is provided by component 112. This calculation of the inverse of the area under the systemic artery dilution curve is then multiplied by the amount or quantity of thermal injectate as is shown by component 114 to obtain the cardiac output or flow. The final calculation is provided by component 116 and is a multiplication of the outputs of components 110 and 114. The output from the component 116 is a measure of the extravascular lung water and is displayed to the user of the system by a visual display device 118. As indicated above, in place of the calculations provided by components 106 and 108 which are the decay times, these calculations may be of the mean time and with these calculations of mean time then used in the subsequent calculations of the system.

It should be appreciated that various corrections may be made for any non-linearities in the thermistors or for any distortions in the curves such as due to a non-zero rise time of the thermistors. In addition, it should be appreciated that the calculations of the area under the curve may also be provided from the pulmonary artery dilution curve instead of the systemic artery dilution curve as shown in calculation 112. It, of course, would also be possible that the cardiac output could be entered into the computer from an external source if this information is available from such external source. Therefore, an external calculation of cardiac output could be used as part of the calculation for a measure of lung water.

It should be appreciated that the calculation of the cardiac output could be made from both the systemic arterial curve and the pulmonary artery curve and that both cardiac outputs could be used in the calculation of lung water as shown in FIG. 7. FIG. 7 illustrates a diagram of a system for providing for a measure of lung water and is similar to FIG. 5 with the addition of calculations represented by components 113, 115 and 117 and a variation in the order in which some calculations are performed. The component 113 provides a calculation of the inverse of the area under the pulmonary artery dilution curve. This calculation is then multiplied by the amount of thermal injectate as shown by component 115. The output from component 115 is the cardiac output calculated from the pulmonary artery ($CO_{PA}$) just as the output of the calculation represented by component 114 is the cardiac output calculated from the systemic artery ($CO_{SA}$). Component 117 represents the multiplication of the cardiac output from the component 115 times the exponential decay time from component 106 just as component 132 represents the multiplication of the cardiac output from component 114 times the exponential decay time from component 108. The final calculation is provided by component 134 which subtracts the output from component 117 from the output from component 132. The output of component 134 is a measure of the extravascular lung water and is displayed to the user on display 118. In place of the calculations provided by components 106 and 108 which are decay times, these calculations may be of the mean time and with these calculations of mean time then used in subsequent calculations of the system.

FIG. 6 illustrates a diagram of a system for providing for a measurement of lung water and including improvements of the present invention in a two-indicator or double dilution system. In FIG. 6, the thermistor 28 provides for a signal which is applied to the analog to digital converter 102 to produce an output signal representative of the changes in temperature or heat concentration. A second indicator such as a concentration of green dye is calculated normally by withdrawing blood from the systemic artery and with an optical device 120 providing for an output signal representative of the concentration of green dye in the systemic artery. This output signal from the optical device 120 is applied as an input signal to an analog to digital converter 122 to produce a signal representative of the change in the concentration of the green dye. The output signals from the analog to digital converters 122 and 102 are applied to a digital computer 124 and with the digital computer including component portions for providing the desired calculations.

Component 108 provides for a calculation of the decay time ($\tau_T$) of the temperature dilution curve in the systemic artery. Component 126 provides for a calculation of the decay time ($\tau_D$) in the green dye dilution curve. A calculation of the inverse of the area under the temperature dilution curve is provided by component 112 and is multiplied by the amount of injectate by component 114 in a similar manner to that shown in the system of FIG. 5. The difference between the decay times is calculated by component 128 and this difference is multiplied by the cardiac output as shown by component 130. The output signal from component 130 is a measure of the extravascular lung water and visual display 118 provides for a display of this measurement of lung water. It is to be appreciated that in place of the calculation of decay times, mean times may be calculated and used with the system of FIG. 6.

The present invention therefore provides for an apparatus and method of measuring or estimating extravascular lung water which involves the use of only one indicator such as heat and with the dilution curve of the indicator being sampled twice. One sampling occurs in the pulmonary artery after the indicator is mixed with the blood before it enters the lungs. The indicator is again sampled in a systemic artery after the indicator has passed through the lungs. The dilution curves which represent the concentration of the indicator as a function of time are measured at these two positions within the body of the subject. The measurements may be made by thermistors mounted at the ends of catheters and with one catheter introduced into a vein and through the right heart and into the pulmonary artery. The second catheter is introduced into a systemic artery.

A characteristic time such as a mean time or a decay time of each of the dilution curves is determined and these characteristic times are multiplied times the blood flow. The difference between these products represents a measure of the extravascular lung water.

The preferred method using only a single indicator requires no pulling of blood from the patient and it has been determined that this method gives results as reproducible as prior art methods and if the characteristic time that is used is the decay time, the results for the measure of lung water have been found to agree well with that determined by measurements of the double dilution technique using green dye and heat as the two indicators.

The present invention also provides for a measurement of the flow or cardiac output which is determined from the dilution curve in the systemic artery. Although this measurement is not as reproducible as that determined from the dilution curve in the pulmonary artery and although this measurement is more susceptible to artifacts, it has been determined that the fluctuations caused by the artifacts in the measurement of the flow from the systemic artery are in the opposite direction as the fluctuations caused by artifacts in the characteristic time of the systemic arterial dilution curve. Therefore, the product of these calculations produces a cancellation of the fluctuations so as to provide for a lung water calculation which is not sensitive to artifacts in the arterial thermal dilution curve.

In addition, if some of the heat indicator is lost to the air in the lungs, the flow measured from the systemic arterial dilution curves is falsely high but the characteristic time of the curve is falsely low. Therefore in the calculation of lung water, which is the product of the flow times characteristic time, a compensation occurs to produce a result which is not as sensitive to losses of indicator as either the characteristic time or the flow.

The present invention, therefore, provides for an improvement even in the standard double dilution method which may use heat as the extravascular indicator, by using the flow or cardiac output determined from the thermal dilution curve in the systemic artery in the computation of lung water.

Although the invention has been described with reference to particular embodiments, it is to be appreciated that various adaptations and modifications may be made and the invention is only to be limited by the appended claims.

I claim:

1. Apparatus for providing a measure of extravascular lung water of a subject using a single thermal indicator, including
   means for providing an injection of the thermal indicator into the bloodstream of the subject at a position proximal to or in the right heart,
   means for detecting a first time-temperature concentration curve of the bloodstream at a position in the pulmonary artery,
   means responsive to the first time-temperature concentration curve detected in the pulmonary artery for calculating a characteristic time for the first time-temperature concentration curve,
   means for detecting a second time-temperature concentration curve of the bloodstream at a position in a systemic artery,
   means responsive to the second time-temperature concentration curve detected in the systemic artery for calculating a characteristic time for the second time-temperature concentration curve,
   means for calculating the flow of blood through the heart and lungs, and
   means for calculating a measure of extravascular lung water in accordance with the product of the blood flow times the difference between the characteristic times for the first and second time-temperature concentration curves.

2. The apparatus for providing a measure of extravascular lung water of claim 1 wherein the means for calculating the characteristic times for the first and second time-temperature concentration curves includes means for calculating the exponential decay times for the curves.

3. The apparatus for providing a measure of extravascular lung water of claim 1 wherein the means for calculating the characteristic times for the first and second time-temperature concentration curves includes means for calculating the mean times for the curves.

4. The apparatus for providing a measure of extravascular lung water of claim 1 wherein the means for calculating the flow of blood calculates the blood flow in accordance with characteristics of the second time-temperature concentration curve of the bloodstream at the position in the systemic artery.

5. The apparatus for providing a measure of extravascular lung water of claim 4 wherein the means for calculating the flow of blood includes means for calculating the blood flow in accordance with the reciprocal of the area under the second time-temperature curve.

6. The apparatus for providing a measure of extravascular lung water of claim 1 wherein the means for detecting the first and second time-temperature concentration curves in the pulmonary and systemic arteries includes catheters for insertion into the pulmonary and systemic arteries and with each catheter including at least one temperature sensitive element.

7. The apparatus for providing a measure of extravascular lung water of claim 1 additionally including means for indicating the measure of extravascular lung water.

8. Apparatus for providing a measure of extravascular lung water of a subject including means for providing an injection of a thermal indicator into the bloodstream of the subject at a position proximal to or in the right heart, including means for detecting the time-temperature concentration curve of the bloodstream at a position in a systemic artery, first means responsive to the time-temperature concentration curve detected in the systemic artery for calculating a characteristic time for the time-temperature curve, second means responsive to the time-temperature concentration curve detected in the systemic artery for calculating the cardiac output in accordance with the reciprocal of the area under the time-temperature curve, and means for calculating a measure of extravascular lung water including the product of the cardiac output times the characteristic time.

9. The apparatus for providing a measure of extravascular lung water of claim 8 wherein the first means for calculating a characteristic time for the time-temperature curve includes means for calculating the exponential decay time for the curve.

10. The apparatus for providing a measure of extravascular lung water of claim 8 wherein the first means for calculating a characteristic time for the time temperature curve includes means for calculating the mean time for the curve.

11. The apparatus for providing a measure of extravascular lung water of claim 8 wherein the means for detecting the time-temperature concentration curve in the systemic artery includes a catheter for insertion into the systemic artery and with the catheter including a temperature sensitive device.

12. The apparatus for providing a measure of extravascular lung water of claim 11 wherein the temperature sensitive device includes a thermistor having resistance values in accordance with the temperature of the bloodstream in the systemic artery.

13. The apparatus for providing a measure of extravascular lung water of claim 8 additionally including means for indicating the measure of extravascular lung water.

14. Apparatus for providing a measure of extravascular lung water of a subject using a single thermal indicator, including means for providing an injection of the thermal indicator into the bloodstream of the subject at a position proximal to or in the right heart, means for detecting a first temperature dilution curve of the bloodstream at a position in the pulmonary artery, means responsive to the first temperature dilution curve detected in the pulmonary artery for calculating a characteristic time for the first temperature dilution curve, means for detecting a second temperature dilution curve of the bloodstream at a position in a systemic artery, p1 means responsive to the second temperature dilution curve detected in the systemic artery for calculating a characteristic time for the second temperature dilution curve, means responsive to a temperature dilution curve of the bloodstream for calculating the flow of blood through the heart and lungs, in accordance with characteristics of the temperature dilution curve, and means for calculating a measure of extravascular lung water in accordance with the difference between the product of the flow times the characteristic time for the first temperature dilution curve and the product of the flow times the characteristic time for the second temperature dilution curve.

15. The apparatus for providing a measure of extravascular lung water of claim 14 wherein the means for calculating the flow of blood is responsive to both the temperature dilution curve in the pulmonary artery and the temperature dilution curve in the systemic artery and the means for calculating a measure of extravascular lung water calculates the difference between the products of the flow calculated from the second dilution curve multiplied by the characteristic time for that curve and the flow calculated from the first dilution curve multiplied by the characteristic time for that curve.

16. The apparatus for providing a measure of extravascular lung water of claim 14 wherein the means for calculating the flow of blood includes means for calculating the blood flow in accordance with the reciprocal of the area under the dilution curve.

17. The apparatus for providing a measure of extravascular lung water of claim 14 wherein the means for calculating the flow of blood includes means for calculating the blood flow in accordance with the second dilution curve detected in the systemic artery.

18. The apparatus for providing a measure of extravascular lung water of claim 17 wherein the means for calculating the flow of blood includes means for calculating the blood flow in accordance with the reciprocal of the area under the dilution curve.

19. The apparatus for providing a measure of extravascular lung water of claim 16 additionally including means for indicating the measure of extravascular lung water.

20. The apparatus for providing a measure of extravascular lung water of claim 14 wherein the means for calculating the characteristic times for the first and second temperature dilution curves includes means for calculating the exponential decay times for the curves.

21. The apparatus for providing a measure of extravascular lung water of claim 14 wherein the means for calculating the characteristic times for the first and second temperature dilution curves includes means for calculating the mean times for the curves.

22. The apparatus for providing a measure of extravascular lung water of claim 14 wherein the means for detecting the first and second temperature dilution curves in the pulmonary and systemic arteries includes catheters for insertion into the pulmonary and systemic arteries and with each catheter including at least one temperature sensitive element.

23. A method of measuring the extravascular lung water of a subject using a single thermal indicator, including the following steps
providing an injection of the thermal indicator into the bloodstream of the subject at a position proximal to or in the right heart,
detecting a first time-temperature concentration curve of the bloodstream at a position in the pulmonary artery,
calculating a characteristic time for the first time-temperature concentration curve,
detecting a second time-temperature concentration curve of the bloodstream at a position in a systemic artery,
calculating a characteristic time for the second time-temperature concentration curve,
providing a calculation for the flow of blood through the heart and lungs, and
calculating a measure of extravascular lung water in accordance with the product of the blood flow times the difference between the characteristic times for the first and second time-temperature concentration curves.

24. The method of measuring the extravascular lung water of claim 23 wherein the characteristic times calculated for the first and second time-temperature concentration curves are the exponential decay times for the curves.

25. The method of measuring the extravascular lung water of claim 23 wherein the characteristic times calculated for the first and second time-temperature concentration curves are the mean times for the curves.

26. The method of measuring the extravascular lung water of claim 23 wherein the calculation for the flow of blood includes calculating the blood flow in accordance with characteristics of the second time-temperature concentration curve of the blood stream at the position in the systemic artery.

27. The method of measuring the extravascular lung water of claim 26 wherein the flow of blood is calculated in accordance with the reciprocal of the area under the second time-temperature curve.

28. The method of measuring the extravascular lung water of claim 23 wherein the detecting of the first and second time-temperature concentration curves in the pulmonary and systemic arteries includes inserting catheters having temperature sensitive elements into the pulmonary and systemic arteries.

29. The method of measuring the extravascular lung water of claim 23 additionally including the step of indicating the measure of extravascular lung water.

30. A method for measuring the extravascular lung water of a subject using a single thermal indicator and with the measure of extravascular lung water calculated from the product of the cardiac output times the difference between characteristic times determined from thermal dilution curves detected in systemic and pulmonary arteries, and with the method including the following steps
providing a first catheter having an opening for injecting the thermal indicator and including a temperature sensitive device,
providing a second catheter including a temperature sensitive device,
inserting the first catheter through the right heart and into the pulmonary artery,
inserting the second catheter into a systemic artery,
injecting the thermal indicator proximal to or in the right heart,
detecting the temperature dilution curve of the bloodstream within the pulmonary artery, and
detecting the temperature dilution curve of the bloodstream within the systemic artery.

31. A method for measuring the extravascular lung water of a subject wherein an injection of a thermal indicator is provided into the bloodstream of the subject at a position proximal to or in the right heart, including the following steps
detecting the time-temperature concentration curve of the bloodstream at a position in a systemic artery,
calculating a characteristic time for the time-temperature curve,
calculating the cardiac output in accordance with the characteristics of the time-temperature curve, and
calculating the measure of extravascular lung water including the product of the cardiac output times the characteristic time.

32. The method for measuring the extravascular lung water of claim 31 wherein the characteristic time calculated for the time-temperature curve is the exponential decay time for the curve.

33. The method for measuring the extravascular lung water of claim 31 wherein the characteristic time calculated for the time-temperature curve is the mean time for the curve.

34. The method for measuring the extravascular lung water of claim 31 wherein the detecting of the time-temperature concentration curve in the systemic artery includes inserting a catheter having a temperature sensitive device.

35. The method for measuring the extravascular lung water of claim 31 additionally including the step of indicating the measure of extravascular lung water.

36. A method for measuring the extravascular lung water of a subject using a single thermal indicator, including
injecting the thermal indicator into the bloodstream of the subject at a position proximal to or in the right heart,
detecting a first temperature dilution curve of the bloodstream at a position in the pulmonary artery,
calculating a characteristic time for the first temperature dilution curve,
detecting a second temperature dilution curve of the bloodstream at a position in a systemic artery,
calculating a characteristic time for the second temperature dilution curve,
calculating the flow of blood through the heart and lungs in accordance with characteristics of a temperature dilution curve, and
calculating a measure of extravascular lung water in accordance with the difference between the product of the blood flow times the characteristic time for the first curve and the product of the blood flow times the characteristic time for the second curve.

37. The method of measuring the extravascular lung water of claim 36 in which the flow of blood through the heart and lungs is calculated from the dilution curve in both the pulmonary artery and systemic artery and the calculation of a measure of extravascular lung water is in accordance with the difference between the product of the flow calculated from the systemic arterial dilution curve times the characteristic time for that curve and the product of the flow calculated from the pulmonary artery curve times the characteristic time for that curve.

38. The method of measuring the extravascular lung water of claim 36 wherein the flow of blood is calculated in accordance with the reciprocal of the area under a dilution curve.

39. The method of measuring the extravascular lung water of claim 36 wherein the calculating of the flow of blood is responsive to the second dilution curve detected in the systemic artery.

40. The method of measuring the extravascular lung water of claim 39 wherein the flow of blood is calculated in accordance with the reciprocal of the area under the dilution curve.

41. The method of measuring the extravascular lung water of claim 36 additionally including the step of indicating the measure of extravascular lung water.

42. The method of measuring the extravascular lung water of claim 36 wherein the characteristic times calculated for the first and second temperature dilution curves are the exponential decay times for the curves.

43. The method of measuring the extravascular lung water of claim 36 wherein the characteristic times calculated for the first and second temperature dilution curves are the mean times for the curves.

44. The method of measuring the extravascular lung water of claim 36 wherein detecting the first and second temperature dilution curves in the pulmonary and systemic arteries includes inserting catheters having temperature sensitive devices into the pulmonary and systemic arteries.

* * * * *